US011730966B2

(12) United States Patent
Pei et al.

(10) Patent No.: US 11,730,966 B2
(45) Date of Patent: Aug. 22, 2023

(54) METHODS, SYSTEMS, AND DEVICES THAT ESTIMATE REMAINING LONGEVITY OF AN IMPLANTED MEDICAL DEVICE WITH IMPROVED ACCURACY

(71) Applicant: PACESETTER, INC., Sylmar, CA (US)

(72) Inventors: Xing Pei, Thousand Oaks, CA (US); Garuda Rachamalla, Canyon Country, CA (US); Jia Qin, Santa Clara, CA (US)

(73) Assignee: Pacesetter, Inc., Sylmar, CA (US)

( * ) Notice: Subject to any disclaimer, the term of this patent is extended or adjusted under 35 U.S.C. 154(b) by 203 days.

(21) Appl. No.: 16/502,973

(22) Filed: Jul. 3, 2019

(65) Prior Publication Data
US 2021/0001129 A1     Jan. 7, 2021

(51) Int. Cl.
*A61N 1/37* (2006.01)
*A61N 1/378* (2006.01)
*A61N 1/372* (2006.01)

(52) U.S. Cl.
CPC ......... *A61N 1/3708* (2013.01); *A61N 1/3704* (2013.01); *A61N 1/378* (2013.01); *A61N 1/37211* (2013.01)

(58) Field of Classification Search
CPC .... A61N 1/3708; A61N 1/378; A61N 1/3704; A61N 1/37211; A61N 1/37252; H02J 7/0048
See application file for complete search history.

(56) References Cited

U.S. PATENT DOCUMENTS 4,768,511 A    9/1988 DeCote, Jr.
5,662,688 A    9/1997 Haefmer et al.
(Continued)

FOREIGN PATENT DOCUMENTS

EP    2250513 B1    1/2014
EP    2219730 B1    1/2015

OTHER PUBLICATIONS

"Method for estimating capacity and predicting remaining useful life of lithium-ion battery" (Chao Hu, Gaurav Jain, Prabhakar Tamirisa, Tom Gorka, Applied Energy, vol. 126, 2014, pp. 182-189) (Year: 2014).*

(Continued)

*Primary Examiner* — Lynsey C Eiseman
*Assistant Examiner* — Ranjani Mari Sundaresan
(74) *Attorney, Agent, or Firm* — Vierra Magen Marcus LLP

(57) ABSTRACT

Described herein are methods, systems, and devices for estimating remaining longevity of an IMD powered by a battery that at any given time has a battery voltage (BV) and a remaining battery capacity (RBC). Such a method can include estimating the RBC using a first technique when the battery is operating within a t least one of one or more plateau regions, estimating the RBC using a second technique, that differs from the first technique when the battery is operating within a decline region, and estimating the remaining longevity of the IMD based on at least one of the estimates of the RBC. Additionally, historical battery data can be stored and used to estimate the RBC, e.g., when the battery is operating within a heavy usage and recovery period. RBC estimation can also depend on whether the IMD is close to its recommended replacement time (RRT).

22 Claims, 8 Drawing Sheets

(56) References Cited

U.S. PATENT DOCUMENTS

| | | | |
|---|---|---|---|
| 5,891,048 A | 4/1999 | Nigam et al. | |
| 6,671,552 B2 | 12/2003 | Merritt et al. | |
| 7,308,311 B2 | 12/2007 | Sorensen et al. | |
| 7,403,813 B1 | 7/2008 | Farazi et al. | |
| 7,941,220 B2 | 5/2011 | Tobacman et al. | |
| 8,004,243 B2 * | 8/2011 | Paryani | G01R 31/3842 320/132 |
| 8,055,343 B2 | 11/2011 | Ghandi et al. | |
| 8,090,566 B2 | 1/2012 | Brown | |
| 8,131,365 B2 | 3/2012 | Zhang et al. | |
| 8,214,164 B2 | 7/2012 | Ghandi et al. | |
| 8,494,633 B2 | 7/2013 | Tobacman et al. | |
| 8,612,167 B2 | 12/2013 | Schmidt et al. | |
| 8,718,771 B2 * | 5/2014 | Gandhi | A61N 1/3627 607/29 |
| 8,761,885 B2 * | 6/2014 | Hussain | G01R 31/392 607/29 |
| 8,868,187 B2 | 10/2014 | Ghandi et al. | |
| 9,616,238 B2 | 4/2017 | Demmer et al. | |
| 9,636,505 B2 | 5/2017 | Sanghera et al. | |
| 10,022,548 B2 | 7/2018 | Brooke et al. | |
| 10,197,629 B2 | 2/2019 | Gordon et al. | |

OTHER PUBLICATIONS

Ellbogen, Kenneth. Clinical Cardiac Pacing, Defibrillation, and Resynchronization Therapy. 3rd ed., Elsevier Health Sciences, 2006. (Year: 2006).*

Zheng et al. Incremental capacity analysis and differential voltage analysis based state of charge and capacity estimation for lithium-ion batteries, Energy, vol. 150, 2018, pp. 759-769, ISSN 0360-5442, https://doi.org/10.1016/j.energy.2018.03.023. (Year: 2018).*

* cited by examiner

METHODS, SYSTEMS, AND DEVICES THAT ESTIMATE REMAINING LONGEVITY OF AN IMPLANTED MEDICAL DEVICE WITH IMPROVED ACCURACY

FIELD OF TECHNOLOGY

Embodiments described herein generally relate to methods, systems and devices that can be used to estimate a remaining longevity of an implantable medical device (IMD).

BACKGROUND

Modern implantable medical devices (IMDs) often provide lifesaving therapy to patients and/or improvements to patients' quality of life. Such IMDs are typically battery powered devices that are implanted within a patient's body to have therapy available to the patient on a continuous basis. One particularly common type of IMD is an implantable cardiac stimulation device.

Implantable cardiac stimulation devices, such as pacemakers and implantable cardioverter/defibrillators (ICD's), are employed to monitor cardiac activity and to provide therapy for patients with a variety of heart arrhythmias. Typically, these IMDs include sensors, that sense heart function and physiological parameters, and waveform generation and delivery systems, that provide electrical waveforms to the heart to correct arrhythmias and to ensure that more proper function of the heart is maintained. Because IMDs are implanted in a patient, it is desirable that the IMDs be as small and lightweight as possible in order to minimize impact on the patient. This is especially the case with leadless pacemakers.

Implantable cardiac stimulation devices are typically provided with batteries to power the monitoring and therapy delivery circuits. Due to the size constraints, the batteries used in implantable cardiac stimulation devices must be very small in size and yet able to provide power over a long period of time. Once the device is implanted, replacement of batteries typically involves invasive surgery. Hence, there is a strong desire to have small batteries that can provide significant power output to power the implantable device for extended periods of time.

It is often important to be able to predict the remaining longevity of a battery powered IMD, and for an external programmer (or another device and/or user interface) to present this projected longevity estimate to a user (e.g., a clinician and/or physician) so that they can make informed clinical decisions. While various methods, systems, and devices exist for predicting the remaining longevity of battery powered IMDs, they typically rely on oversimplifications that introduce errors into remaining longevity predictions.

One indicator of an IMD's remaining longevity is the time to the Recommended Replacement Time (RRT), which is one of the key pieces of information used to assess the functionality of an IMD. Healthcare providers often use the RRT to schedule patients for follow-up appointments and assess when to schedule patients for device replacement surgery, due to the estimated battery remaining longevity.

The accuracy of a remaining longevity estimate, such as the time to RRT, is particularly important in healthcare planning for patients with an implantable cardiac defibrillation (ICD) device. For example, a healthcare provider may just schedule routing follow-up visits when an estimated longevity is far from the RRT, the healthcare provider may schedule more frequent visits when the device is approaching its RRT, and the healthcare provider may schedule device replacement surgery when the device is very close to its RRT, at its RRT, or post RRT.

Inaccurate remaining longevity estimates put a burden on healthcare providers since inaccurate estimates may require more unnecessary frequent monitoring of the patient and interrupt scheduling or planned healthcare activities, or may require urgent intervention since the device is unexpectedly at its RRT or post RRT. Further, earlier than necessary frequent follow-up visits and/or device replacement surgery may increase overall healthcare costs, while a later than needed device replacement surgery can put a patient at risk of not receiving adequate therapies.

In view of the above, it would be desirable to provide methods, systems, and devices that provide more accurate predictions of IMD remaining longevity.

SUMMARY

Certain embodiments of the present technology are directed to methods, devices, and systems for estimating a remaining longevity of an IMD powered by a battery that at any given time has a battery voltage (BV) and a remaining battery capacity (RBC). A performance profile for such a battery, which specifies a relationship between the BV and the RBC, includes one or more decline regions and one or more plateau regions, wherein within each of the one or more decline regions a rate at which the BV decreases as the RBC decreases exceeds a rate threshold, and wherein within each of the one or more plateau regions the rate at which the BV decreases as the RBC decreases does not exceed the rate threshold. In accordance with certain embodiments, a method comprises: estimating the RBC using a first technique when the battery is operating within at least one of the one or more plateau regions; estimating the RBC using a second technique, that differs from the first technique, when the battery is operating within at least one of the one or more decline regions; and estimating the remaining longevity of the IMD based on at least one of the estimates of the RBC. In accordance with certain embodiments, the one or more of the methods summarized herein is/are performed by an external device that wirelessly communicates with the IMD for which the remaining longevity is being estimated.

In accordance with certain embodiments, using the first technique to estimate the RBC comprises estimating the RBC based on a weighted average of a remaining capacity as a function of the BV and a remaining capacity as a function of consumption; and using the second technique to estimate the RBC comprises estimating the RBC based on the remaining capacity as a function of consumption. Additionally, a third technique can be used to estimate the RBC as a function of battery voltage (BV).

Each of the decline and plateau regions has a corresponding battery voltage range ($BV_{range}$) that extends from a start of the battery voltage range ($BV_{start\ of\ range}$) to an end of the battery voltage range ($BV_{end\ of\ range}$). In accordance with certain embodiments, estimating the RBC based on the weighted average of the remaining capacity as a function of the BV and the remaining capacity as a function of consumption is performed using the following equation:

$$RBC = \frac{(BV - BV_{end\ of\ range}) * RC(C) + (BV_{start\ of\ range} - BV) * RC(BV)}{BV_{range}}$$

where RBC is the remining battery capacity, RC(BV) is the remining capacity as a function of the BV, RC(C) is the remining capacity as a function of consumption, $BV_{start\ of\ the\ range}$ is the BV at the start of the $BV_{range}$, $BV_{end\ of\ the\ range}$ is the BV at the end of the $BV_{range}$, and $BV_{range}$ is a voltage difference between the $BV_{start\ of\ the\ range}$ and the $BV_{end\ of\ the\ range}$.

In accordance with certain embodiments, the estimating the RBC based on the remaining capacity as a function of consumption (RC(C)) is performed using the following equation:

$$RBC = RC(BV)$$

where RBC is the remining battery capacity, and RC(BV) is the remining capacity as a function of the BV.

In accordance with certain embodiments, the consumption (C) comprises an initial capacity minus a used capacity, wherein the used capacity comprises a summation of the following: consumption during manufacturing and testing; consumption during shelf-time; consumption during implant; and consumption postimplant to a present date.

In accordance with certain embodiments, the first technique is used to estimate the RBC when the battery is operating within at least one of the one or more plateau regions and the BV is above a voltage threshold, wherein the BV being above the voltage threshold is indicative of the IMD being far from a recommended replacement time (RRT). Such embodiments can further comprise estimating the RBC using a third technique, that differs from the first and second techniques, when the battery is operating within at least one of the one or more plateau regions and the BV is below the voltage threshold, wherein the BV being below the voltage threshold is indicative of the IMD being close to the RRT. In accordance with certain embodiments, the IMD stores historical battery data from time-to-time, the historical battery data including at least one of a historical battery voltage ($BV_{hist}$) or a historical remaining battery capacity ($RC_{hist}$). In certain such embodiments, the third technique that is used to estimate the RBC estimates the RBC based on the stored historical battery data. In accordance with certain embodiments, using the third technique to estimate the RBC further comprises determining current (i.e., present) battery data, wherein the current battery data includes at least one of a current (i.e. present) battery voltage ($BV_{current}$) or a current (i.e., present) remaining capacity ($RC_{current}$), and estimating the RBC also based on the current battery data.

In certain embodiments, during a heavy battery usage and recovery period (during which a current battery voltage ($BV_{current}$) is not indicative of the RBC), the RBC is estimated based on a most recent instance of the historical battery data (which was stored prior to the heavy battery usage and recovery period, and thus was unaffected by the heavy battery usage and recovery period) and based on a consumption between a time of the most recent instance of the historical battery data (that was unaffected by the heavy battery usage and recovery period) and a current (i.e., present) time.

In accordance with certain embodiments of the present technology, estimating the remaining longevity of the IMD based on at least one of the estimates of the RBC comprises: estimating a total future consumption; and estimating the remaining longevity of the IMD using the following equation:

$$\text{remaining longevity} = \frac{RBC}{\text{Future (use)}}$$

where remaining longevity is the remaining longevity of the IMD, RBC is a most recent estimate of the RBC; and Future (use) is the estimated total future consumption.

Certain embodiments of the present technology are directed to an external device configured to estimate a remaining longevity of an IMD powered by a battery that at any given time has a BV and an RBC. Such an external device can include a telemetry subsystem, at least one processor, and a user interface (e.g., display). The telemetry subsystem is configured to wirelessly communicate with an IMD and thereby obtain measurements of a BV from the IMD. The at least one processor (e.g., of a controller of the IMD) is communicatively coupled to the telemetry subsystem and configured to estimate the RBC using a first technique when the battery of the IMD is operating within at least one of one or more plateau regions; estimate the RBC using a second technique, that differs from the first technique, when the battery of the IMD is operating within at least one of one or more decline regions; and estimate the remaining longevity of the IMD based on at least one of the estimates of the RBC. The user interface, e.g., a display, is configured to output the estimate of the remaining longevity of the IMD. Such an external device can be, e.g., an external clinical programmer, an in-home monitor, or a mobile computing device, but is not limited thereto. The estimate of the remaining longevity can be displayed, printed, and/or auditorily output, but is not limited thereto.

In accordance with certain embodiments, the at least one processor of the external device is configured to use the first technique to estimate the RBC when the battery is operating within at least one of the one or more plateau regions and the BV is above a voltage threshold, wherein the BV being above the voltage threshold is indicative of the IMD being far from a recommended replacement time (RRT). Additionally, the at least one processor is configure to: estimate the RBC using a third technique, that differs from the first and second techniques, when the battery is operating within at least one of the one or more plateau regions and the BV is below the voltage threshold, wherein the BV being below the voltage threshold is indicative of the IMD being close to the RRT. Additionally, the at least one processor of the external device is configured to estimate the RBC using a fourth technique when the battery is operating in a heavy battery usage and recovery period (during which a current battery voltage ($BV_{current}$) is not indicative of the RBC), wherein using the fourth technique involves estimating the RBC based on a most recent instance of a historical battery data (which was stored prior to the heavy battery usage and recovery period, and thus was unaffected by the heavy battery usage and recovery period) and based on a consumption between a time of the most recent instance of the historical battery data (that was unaffected by the heavy battery usage and recovery period) and a current (i.e., present) time.

In accordance with certain embodiments, the at least one processor of the external device is configured to determine whether the battery of the IMD is operating within a said plateau region or a said decline region based on one or more measurements of the BV obtained from the IMD.

In accordance with certain embodiments, the user interface of the external device comprises a display, and the at least one processor of the external device is configured to produce and display, on the display of the external device, a trending graph that shows the estimated RBC at a plurality of different times verses a time since implant of the IMD, wherein the trending graph includes one or more indications of when a period of heavy usage occurred or when a programming change occurred.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

As noted above, it is often important to be able to predict the remaining longevity of a battery powered IMD, and for an external programmer (or another device and/or user interface) to present this projected longevity estimate to a user (e.g., a clinician and/or physician) so that they can make informed clinical decisions. While various methods, systems, and devices exist for predicting the remaining longevity of battery powered IMDs, they typically rely on oversimplifications that introduce errors into longevity predictions. Accordingly, it would be desirable to provide methods, systems, and devices that provide more accurate predictions of IMD longevity. Battery powered IMDs are also referred to herein more succinctly as IMDs, or simply as devices, which should be understandable from the context in which these terms are used.

Figure 1A:
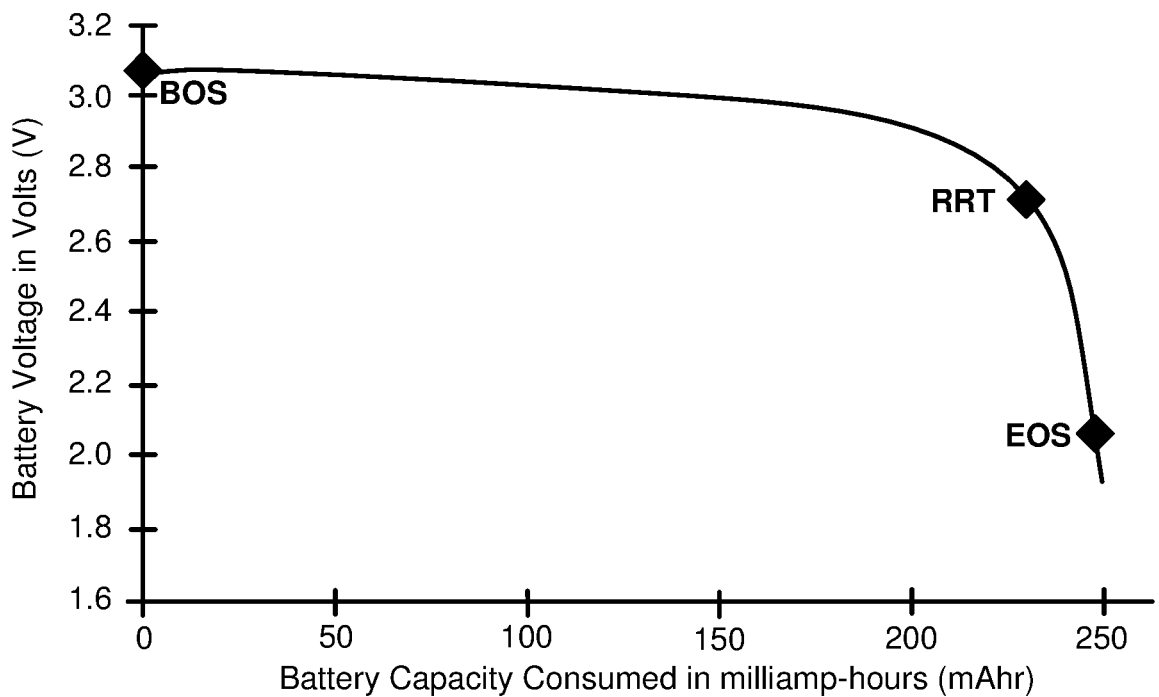
FIG. 1A illustrates an exemplary performance profile curve for an exemplary battery that is designed for an IMD, where the performance profile plots battery voltage (BV) versus battery capacity consumed.
Figure 1B:
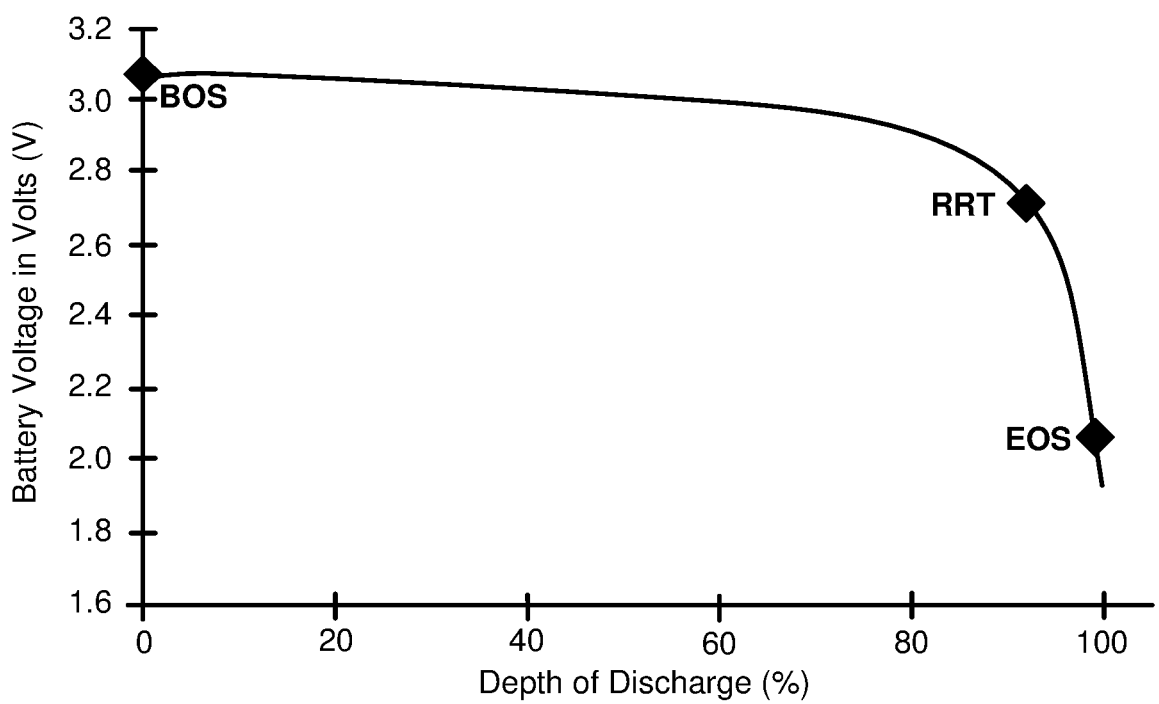
FIG. 1B illustrates an equivalent performance profile curve for the same exemplary battery, where the performance profile plots battery voltage (BV) versus depth of discharge.

Batteries are electrochemical systems that establish a voltage between two poles that can supply current through an external load. One means of characterizing the capabilities of a battery is via a performance profile, which plots battery voltage (BV) versus relative depth of discharge (or absolute battery capacity consumed or another equivalent metric) for a given external load, rate of discharge, etc. FIG. 1A illustrates an exemplary performance profile curve for an exemplary battery that is designed for an IMD, where the performance profile plots BV versus battery capacity consumed. FIG. 1B illustrates an equivalent performance profile curve for the same exemplary battery, where the performance profile plots BV versus depth of discharge. A few key fiducial battery stages are labeled in FIGS. 1A and 1B, including the Beginning of Service (BOS), Recommended Replacement Time (RRT), and End of Service (EOS). The BOS, which also referred to as the Beginning of Life (BOL), is the nomenclature for a new battery that has not been significantly used. The RRT, which is also known as the Elective Replacement Indicator (ERI) or Elective Replacement Time (ERT), is the nomenclature for the time at which it is recommended that a battery be replaced within a specified period of time (also known as the Prolonged Service Period (PSP)) (e.g., six months). The EOS, which is also known as the End of Life (EOL) or End of Service Live (EOSL), is the nomenclature for an old battery that has been depleted to the point that it could no longer reliability support basic functions. The RRT for a battery (or more generally a battery powered IMD) can occur, e.g., approximately six months prior to the EOS for the battery (or more generally, the battery powered IMD).

Referring to FIGS. 1A and 1B, the positions of the fiducials BOS, RRT, and EOS may not be inherent features of the battery, but rather may be selected by the designers based on performance requirements, and/or the like, of the IMD that the battery is powering. Thus, for example, with an EOS voltage selected at 2.1V, the total usable charge capacity (from BOS to EOS) of the battery represented in FIG. 1A is approximately 248 mAhr.

In principle, a remaining longevity estimate can be calculated by dividing a remaining usable battery capacity by a projected future usage. Therefore, the accuracy of such a remaining longevity estimate relies on two factors (1) the remaining usable battery capacity and (2) the projected future usage.

To increase device longevity and to improve the ability to provide stronger and timely therapy, there have been lot of improvements made to the batteries used in IMDs. Consequently, these batteries make the estimation of remaining longevity even more challenging. This is especially the case where the remaining usable battery capacity is not a linear function to the battery voltage (BV), or even a monophasic function. For example, the BV, which is often used for calculating the remaining usable battery capacity for use in a longevity estimate, varies depending not only on the IMD usage, but also on the timing of a BV measurement after certain IMD usage. It becomes a complex function—

$$\text{Battery Voltage } (t) = f(\text{background usage}, \text{transient usage(function of time)}, \text{timing of battery measurement}). \quad \text{Eq1:}$$

Figure 2:
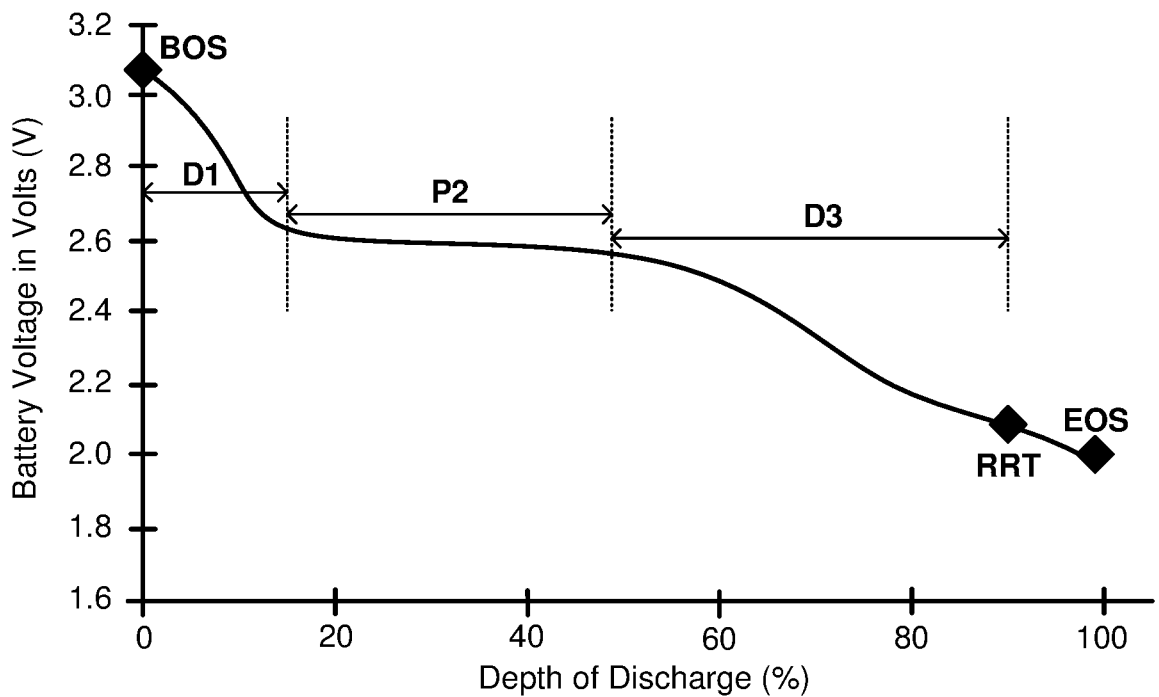
FIG. 2 shows an exemplary performance profile for a Q High Rate battery.
Figure 3:
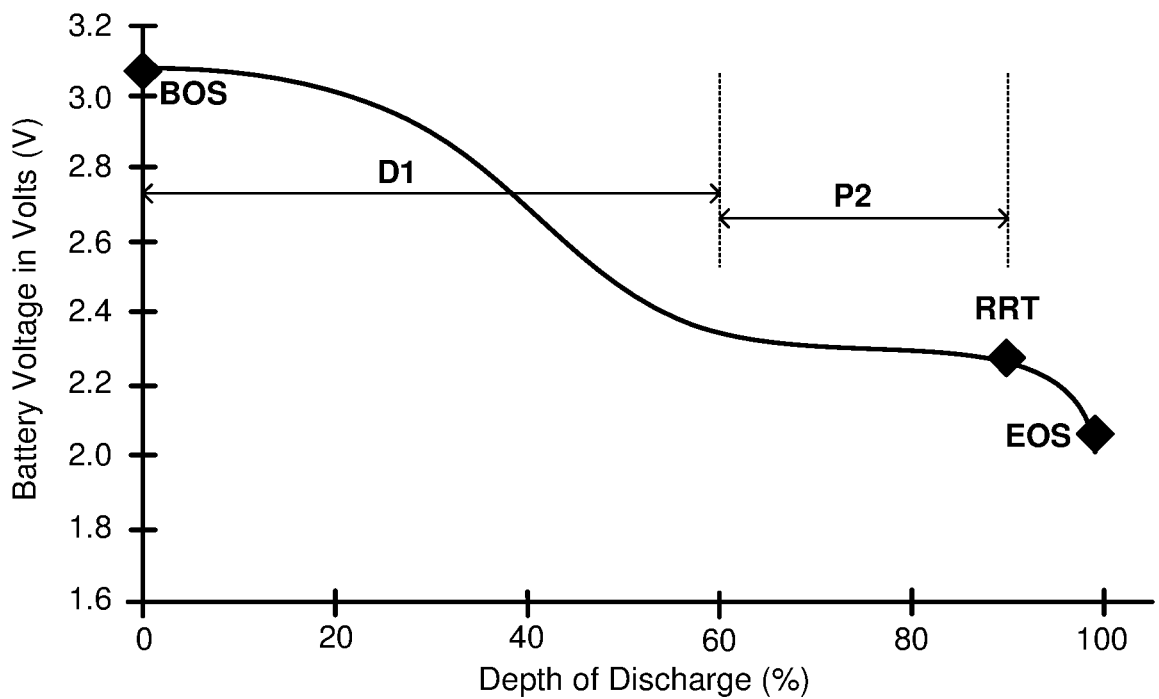
FIG. 3 shows an exemplary performance profile for a lithium-silver vanadium oxide (Li/SVO) battery or a lithium carbon monofluoride (Li—CFx) battery.
Figure 4:
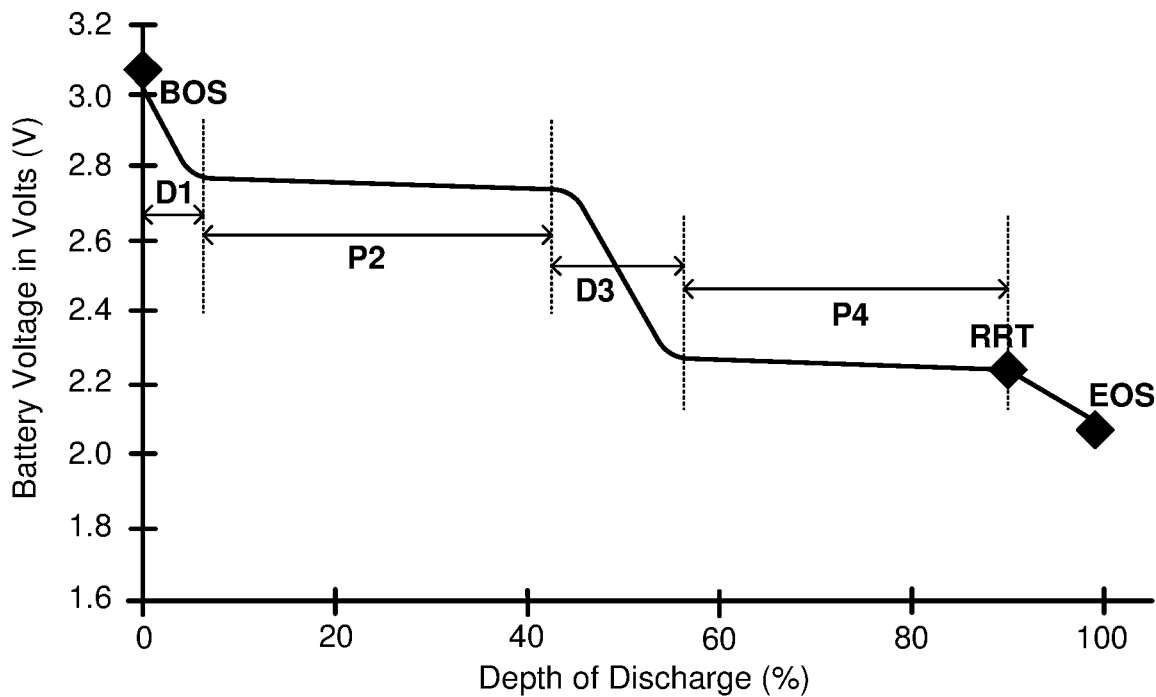
FIG. 4 shows an exemplary performance profile for a potential future developed type of battery.

The graphs in FIGS. 2, 3, 4 show exemplary performance profiles of the battery capacity (BC) versus battery voltage (BV) for three different exemplary battery types. More specifically, FIG. 2 shows an exemplary performance profile for a QHR™ (Q High Rate) battery. FIG. 3 shows an exemplary performance profile for a lithium-silver vanadium oxide (Li/SVO) battery or a lithium carbon monofluoride (Li—CFx) battery. FIG. 4 shows an exemplary performance profile for a potential future developed type of battery. The battery profiles shown in FIGS. 2-4 each include generally flat regions where battery capacity decrease over time while the battery voltage (BV) varies little. These generally flat regions, which also referred to herein as "plateau regions", may occur where device capacity is far away from the RRT (corresponding to a higher BV) or close to the RRT (corresponding to a lower BV). The battery performance profiles shown in FIGS. 2, 3, and 4 also each include regions where both battery capacity and battery voltage (BV) simultaneously decrease over time, which regions are referred to herein as "decline regions". More specifically, within the decline region(s) a rate at which the BV decreases as the RBC decreases exceeds a rate threshold, and within the plateau region(s) the rate at which the BV decreases as the RBC decreases does not exceed the rate threshold. Explained another way, within the decline regions(s) a downward slope of the performance profile curve exceeds a threshold, and within the plateau region(s) the downward slope of the performance provide curve does not exceed the threshold.

In FIGS. 2-4, the various decline and plateau regions are labeled alphanumerically, with the letter "D" referring to decline regions, and the letter "P" referring to plateau regions. For example, the performance profile in FIG. 2 includes a decline region D1, followed by a plateau region P2, followed by a decline region D3. The performance profile in FIG. 3 includes a decline region D1 followed by a plateau region P2. The performance profile in FIG. 4 includes a decline region D1, followed by a plateau region P2, followed by a decline region D3, followed by a plateau region D4. Accordingly, as can be appreciated from FIG. 4, a future battery with more complex battery chemistry may have multiple plateau regions (P2 and P4).

Figure 5:
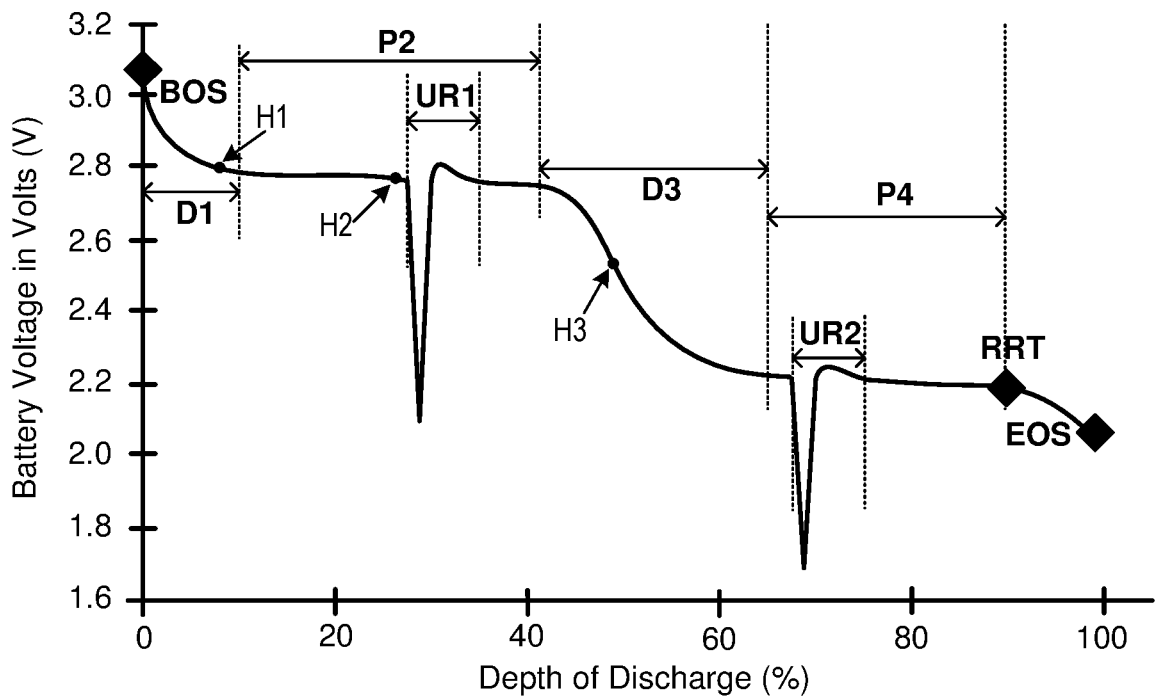
FIG. 5 illustrates how a battery voltage (BV) may be affected during heavy usage and recover periods, during which periods, the BV is not an accurate indicator of remaining longevity of an IMD including the battery.

Moreover, the BV after a heavy usage, such as a high voltage charging, may temporarily dip and then recover (to an even higher voltage than before the heavy use) before it returns to the expected BV at that battery capacity, as shown for example in FIG. 5. These non-linear behaviors associated with heavy usage and recover periods, e.g., labelled UR1 and UR2 in FIG. 5, makes it difficult to use the BV to predict the remaining battery longevity. Heavy battery usage and recovery periods can occur during and following charging of one or more capacitors (e.g., for use in delivery defibrillation and/or other high voltage therapy), during and following performance of telemetry, and/or during and following performance of patient notifications, but is not limited thereto. The length of a heavy battery usage and recovery period, which can also be referred to more succinctly as a use and recovery (UR) period, can depend on the specific type of heavy battery usage and the degree of the usage. For example, a UR period corresponding to charging one or more defibrillator capacitor(s) can last 20 days, a UR period corresponding to telemetry can last for 5 days, a UR period corresponding to a vibratory patient notification can last 10 hours, and a UR period corresponding to an auditory patient notification can last for 5 hours. These are just examples which are not intended to be limiting.

Conventionally, IMDs and/or external programmers have relied solely or at least primarily on measures of the BV for the triggering of the RRT. However, the characterization complexity of the BV also complicates the RRT triggering, because of the variation in the BV as a function of time, as can be appreciated from Eq1 above. Accordingly, in certain situations, measures of the BV do not provide for accurate triggering of the RRT.

In addition, some advanced IMDs utilize Bluetooth Low Energy (BLE) communication technology for long range wireless communication. In comparison to the Medical Implant Communication Service (MICS) RF communication technology used by many previous and existing IMDs, the BLE communication technology relies on an IMD transmitting active advertising signals (in comparison to an IMD performing passive listening to signals when an IMD relies on MICS RF communication technology). This new advanced BLE communication can further complicate the calculation of the projected future usage, due to variations in the advertising scheme based on the use conditions.

Certain embodiments of the present technology described herein deal with the above mentioned challenges holistically with self-adjustments to provide for better accuracy for remaining longevity estimates and RRT triggering. In accordance with certain embodiments, remaining longevity estimates are based on multiple factors, including, but not limited to, whether the battery is operating in a decline region or a plateau region, whether the battery is far from or close to the RRT, whether the battery is operating within a heavy usage and recovery period, a remaining usable battery capacity, and/or a projected future usage, wherein the remaining longevity can be a quotient of the remaining usable battery capacity divided by the projected future usage.

When an IMD is manufactured, a value for a total battery capacity to the RRT is typically provided by the IMD manufacturer, which value is considered a constant. However, due to variations in the manufacturing process, the actual total battery capacity to the RRT for different instances of the same type of IMD will vary, which contributes to inaccurate remaining longevity projections as well. In accordance with certain embodiments of the present technology, this inaccuracy is compensated for using self-adjustments, as will be described below.

In accordance with certain embodiments of the present technology, the full battery capacity is divided into several regions based on battery performance profile curve characteristics, in particular, to distinguish the plateau regions (within which the BV barely drops) from decline regions (within which the BV significantly drops) when battery capacity is consumed. Exemplary plateau regions are labeled with the letter "P" followed by a number in FIGS. 2-4, introduced above, as well as in FIG. 5. Exemplary decline regions are labeled with the letter "D" followed by a number in FIGS. 2-4, introduced above, as well as in FIG. 5. For example, FIG. 4 shows decline regions D1 and D3, and plateau regions P2 and P4.

In accordance with certain embodiments of the present technology, the total consumption to date is a summation of the following capacity consumptions during different phases of device life cycle: consumption during manufacturing and testing; consumption during shelf-time; consumption during implant; and consumption postimplant to date. In each of just mentioned phases of device life cycle, where applicable, the consumption includes: (1) the base housekeeping current; (2) pacing and/or sensing current; (3) algorithm current; (4) the current used for high voltage therapy and battery maintenance and capacitor maintenance; and (5) the current used for communication (i.e., telemetry) with one or more external devices. Due to the measurement inaccuracy of the current drains, the errors of each measurement can be accumulated over the lifetime of the device usage. In accordance with certain embodiments of the present technology, this inaccuracy is compensated for using self-adjustments, as will be described below.

In accordance with certain embodiments of the present invention, BV measurements are made and stored from time-to-time, and during certain periods of time, the RBC is estimated based on a BV measurement and battery performance profile curve information, e.g., stored in a look-up-table (LUT). Such BV measurements can be made periodically, e.g., once per month, once per week, or once per day, but not limited thereto. Alternatively, or additionally, such BV measurements can be made in response to one or more triggering events, e.g., a BV measurement can be made and stored just before delivery of defibrillation and/or another type of high voltage therapy, just before performance of telemetry, and/or just before performance of a patient notification. Due to sampling errors, the flatness of a battery performance profile curve within plateau regions(s), and use history, the accuracy of the estimates for the RBC varies at the different regions of the battery performance profile curve. In accordance with certain embodiments of the present technology, this inaccuracy is compensated for using self-adjustments, as will be described below.

In accordance with certain embodiments of the present technology, at each point in time, of a plurality of temporally spaced apart points in time, usage data up to the point in time and a BV measurement at that point in time are stored within memory of an IMD as historical data. Such historical data can be available for uploading to an external device that determines estimates of RBC, and more generally, determines estimates of remaining longevity. In certain embodiments, the usage data up to the point in time can include separately, or a summation of: (1) the consumption of the base housekeeping current up to the point in time; (2) the consumption of the pacing and/or sensing current up to the point in time; (3) the consumption of the algorithm current up to the point in time; (4) the consumption of the current used for high voltage therapy and battery maintenance and capacitor maintenance up to the point in time; and (5) the consumption of the current used for communication (i.e., telemetry) with one or more external devices up to the point in time, wherein high power telemetry, mid power telemetry and low power telemetry consumption are summed. Such historical data can be determined and stored at specific points associated with a battery performance profile curve, such as during or close to transitions between decline and plateau regions, and/or prior to and/or following periods of heavy use and recovery. Exemplary points at which historical data may be determined and stored are labeled H1, H2, and H3 in FIG. 5. Such points at which historical data is determined and stored can be referred to generically as Hn points. Historical data will likely be stored at many more data points than the exemplary labeled data points, and may be stored on some schedule, e.g., once per hour, per day, per week, etc., but is not limited thereto, and/or in response to a triggering event.

In addition, in accordance with certain embodiments of the present technology, a floating and lock feature is used for historical data (Hn) collection. For example, after entering the D3 region, if the most recent BV measurement is not affected by the heavy usage (i.e., does not coincide with a UR period)—that BV measurement can be directly used for a remaining capacity calculation, and then the current (Hn) is the latest historical point. By contrast, if the most recent BV measurement is affected by the heavy usage (i.e., coincides with a UR period)—that BV measurement cannot be directly used for a remaining capacity calculation, in which case the (Hn) is not updated; and the latest (i.e., most recent) historical point that is not affected by the heavy usage is kept until it reaches the H3 point, then the historical data point can be locked for use until the UR period is over. Further details of how to use historical data to estimate RBC, or more generally remaining longevity, during a UR period is discussed below.

Figure 6:
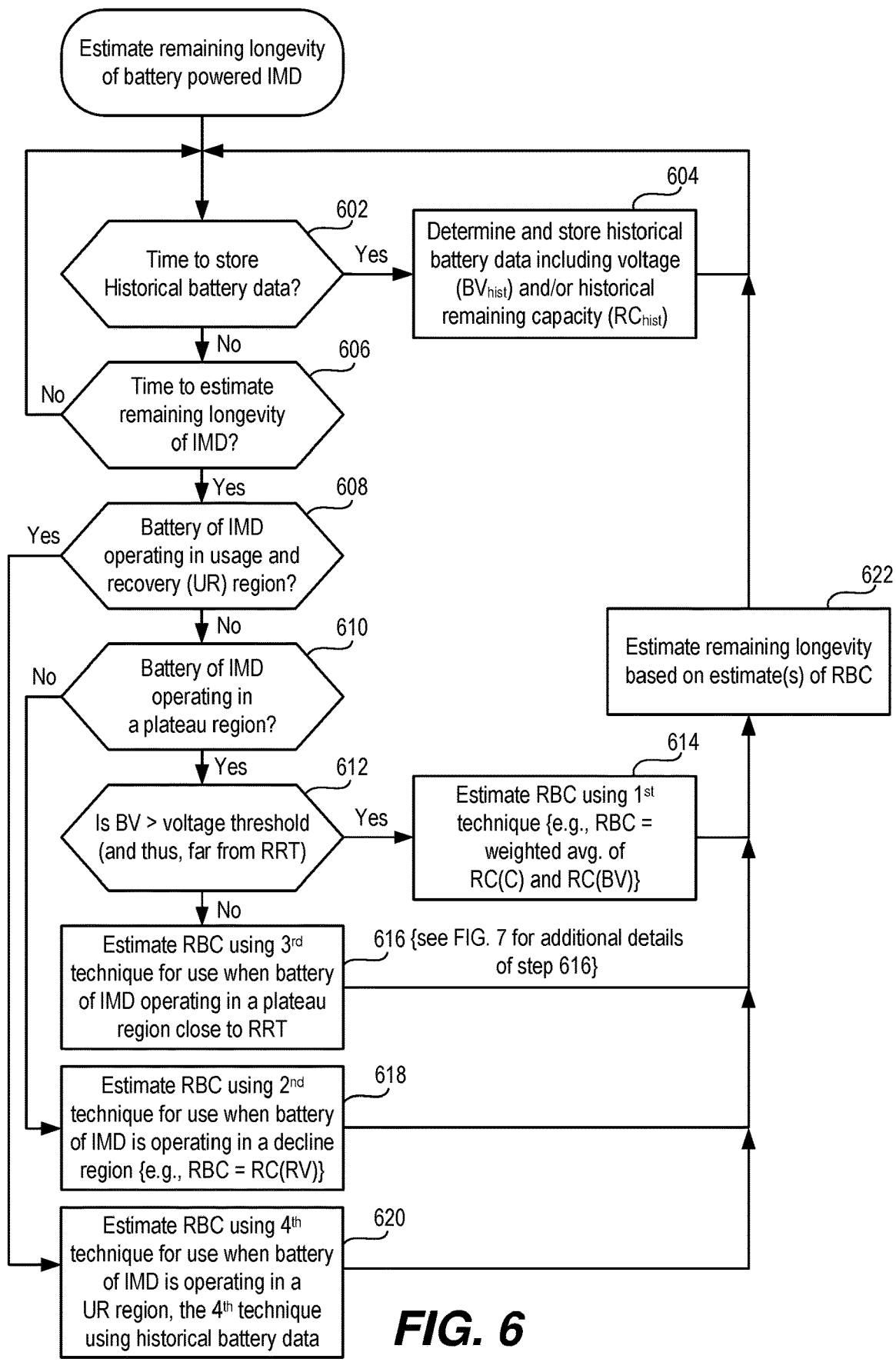
FIG. 6 is a high level flow diagram that is used to summarize methods for estimating the remaining longevity of an IMD in accordance with certain embodiments of the present technology.

The high level flow diagram of FIG. 6 will now be used to summarize methods for estimating the remaining longevity of an IMD in accordance with certain embodiments of the present technology. In the description herein, the term "remaining longevity" is sometimes referred to more succinctly as "longevity".

Referring to FIG. 6, at step 602 there is a determination of whether it is an appropriate time at which to store historical battery data. Historical battery data can be stored periodically, e.g., once per day, once per week, or once per month, but is not limited thereto. Additionally, or alternatively, historical battery data can be stored in response to a triggering event. For an example, historical battery data can be stored just before a heavy battery usage and recovery (UR) period is about to occur and/or the UR period is over. If the answer to the determination at step 604 is Yes, then flow goes to step 604, at which step historical battery data is determined and stored in memory of the IMD (e.g., memory 1060 in FIG. 10). In certain embodiments, the historical battery data includes historical battery voltage ($BV_{hist}$) and/or a historical remaining battery capacity ($RC_{hist}$), but is not limited thereto. Additionally, or alternatively, the historical battery data can include data indicative of the total consumption to date and/or individual types of consumption to date. If the answer to the determination at step 602 is No, then flow goes to step 606.

At step 606 there is a determination of whether it is an appropriate time to estimate a remaining longevity of the IMD. The remaining longevity of the IMD can be determined, for example, when a patient in which the IMD is implanted visits a clinician and the IMD is being interrogated using an external clinical programmer. Alternatively, or additionally, the remaining longevity of the IMD can be determined periodically (e.g., once per month, but not limited thereto) by an external patient monitor (e.g., a bedside monitor) or by a remote server that communicates with the external patient monitor. If the answer to the determination at step 606 is No, then flow returns to step 602. If the answer to the determination at step 606 is Yes, then flow goes to step 608.

At step 608 there is a determination of whether the battery of the IMD is operating in a heavy battery usage and recovery period. Heavy battery usage and recovery periods can occur during and following charging of one or more capacitors (e.g., for use in delivery defibrillation and/or other high voltage therapy), during and following performance of long telemetry sessions, and/or during and following performance of patient notifications, but is not limited thereto. The length of a heavy battery usage and recovery period, which can also be referred to more succinctly as a use and recovery (UR) period, can depend on the specific type of heavy battery usage and the usage itself. For example, a UR period corresponding to charging one or more defibrillator capacitor(s) can last 20 days, a UR period corresponding to telemetry can last for 5 days, a UR period corresponding to a vibratory patient notification can last 10 hours, and a UR period corresponding to an auditory patient notification can last for 5 hours, which examples were also mentioned above. These are just examples which are not intended to be limiting. One or more timers implemented in software, hardware, and/or firmware can be triggered and used to determine whether the battery of the IMD is operating within a UR period, and thus, within a UR region. If the answer to the determination at step 608 is Yes, then flow goes to step 620, which is discussed below. If the answer to the determination at step 608 is No, then flow goes to step 610.

At step 610 there is a determination of whether the battery of the IMD is operating in a plateau region. As can be appreciated from FIGS. 2-5 discussed above, each of the plateau regions has a corresponding battery voltage range ($BV_{range}$) that extends from a start of the battery voltage range ($BV_{start\ of\ range}$) to an end of the battery voltage range ($BV_{end\ of\ range}$). Similarly, each of the decline regions has a corresponding $BV_{range}$. For example, referring back to FIG. 4, the decline region D1 has a corresponding to a first $BV_{range}$, the plateau region P2 has a corresponding to a second $BV_{range}$, the decline region D3 has a corresponding to a third $BV_{range}$, and the plateau region P4 has a corresponding to a fourth $BV_{range}$. Such BV ranges can be stored in memory of an IMD and/or an external device. In accordance with certain embodiments, step 610 is performed by comparing a present BV to the various potential BV ranges within which the battery of the IMD may be operating.

If the answer to the determination at step 610 is No, meaning the battery of the IMD is not operating in a plateau region, but rather is operating in a decline region, then flow goes to step 618 at which a second technique is used to estimate the RBC. Additional details of the second technique used to estimate the RBC at step 618, are discussed below. If the answer to the determination at step 610 is Yes, meaning the battery of the IMD is operating in a plateau region, then flow goes to step 612, at which there is a determination of whether or not the battery of the IMD is close to the RRT.

More specifically, at step 612 there is a determination of whether the BV is greater than a voltage threshold, and thus, far from the RRT. If the answer to the determination at step 612 is Yes, meaning the BV is in a plateau region and far from the RRT, then flow goes to step 614. At step 614 the RBC is estimated using a first technique. If the answer to the determination at step 612 is No, meaning the BV is operating in a plateau and close to the RRT, then flow goes to step 616. At step 616 (when the BV is close to the RRT) the RBC is estimated using a third technique, which differs from the first technique used at step 614 and from the second technique used at step 618.

In accordance with certain embodiments, the first technique used to estimate the RBC at step 614 (while the battery of the RRT is operating in a plateau region and far from the RRT) involves estimating the RBC based on a weighted average of a remaining capacity as a function of the BV (RC(BV)) and a remaining capacity as a function of consumption (RC(C)). In accordance with specific embodiments, the first technique, which is used at step 614 to estimate the RBC, uses the following Equation:

$$RBC = \frac{(BV - BV_{end\ of\ range}) * RC(C) + (BV_{start\ of\ range} - BV) * RC(BV)}{BV_{range}}$$

where
RBC is the remining battery capacity,
RC(BV) is the remining capacity as a function of the BV,
RC(C) is the remining capacity as a function of consumption,
$BV_{start\ of\ the\ range}$ is the BV at the start of the $BV_{range}$,
$BV_{end\ of\ the\ range}$ is the BV at the end of the $BV_{range}$, and
$BV_{range}$ is a voltage difference between the $BV_{start\ of\ the\ range}$ and the $BV_{end\ of\ the\ range}$.

After the RBC is estimated at step 614 using the first technique then flow goes to step 622, at which the remaining capacity is estimated based on the estimated RBC. In accordance with certain embodiments, the remaining longevity of the IMD is estimated at step 622 using the following Equation:

$$\text{remaining longevity} = \frac{RBC}{\text{Future (use)}}$$

where
RBC is a most recent estimate of the RBC; and
Future (use) is the estimated total future consumption.
The exemplary future consumption may include housekeeping current, pacing current and sensing current based on the patient usage history and based on the base programming, capacitor maintenance current, battery maintenance current, estimated telemetry usage for in clinical visits, and estimated telemetry usage for remote care (such as the advertising of the BLE telemetry, daily check, and/or weekly trend data, etc.).

Returning to the discussion of step 610, if the answer to the determination at step 610 is No, meaning the battery of the IMD is operating in a decline region, then flow goes to step 618 at which the second technique is used to estimate the RBC. In accordance with certain embodiments, the second technique, which is used to estimate the RBC at step 618, involves estimating the RBC based on the remaining capacity as a function of consumption (RC(C)). The consumption, i.e., C, can be determined using an algorithm, and the remaining capacity as a function of consumption, i.e., RC(C), can be determined using a look-up-table (LUT) and/or an algorithm, such as an interpolation algorithm, but is not limited thereto. The remaining capacity can alternatively be determined as a function of battery voltage and base current, i.e., RC(BV,I), where BV is the battery voltage, and I is the base current. In accordance with certain embodiments, the consumption is equal to an initial capacity of the battery of the IMD minus a used capacity of the battery of the IMD, wherein the used capacity can be a summation of the following: consumption during manufacturing and testing; consumption during shelf-time; consumption during implant; and consumption postimplant to a present date. In accordance with certain embodiments, estimating the RBC based on the remaining capacity as a function of consumption (RC(C)) at step 618 can be performed using the following Equation:

RBC=RC(BV)

where
RBC is the remining battery capacity, and
RC(BV) is the remining capacity as a function of the BV.

Returning to the discussion of step 612, if the answer to the determination at step 612 is No, meaning the BV is operating in a plateau and close to the RRT, then flow goes to step 616 at which a third technique is used to estimate the RBC. In accordance with certain embodiments, the third technique that is used to estimate the RBC at step 616 estimates the RBC based on stored historical battery data as well as current (i.e., present) battery data. Additional details of step 616, according to specific embodiments of the present technology, are described below with reference to the high level flow diagram of FIG. 7. After the RBC is estimated at step 616 using the third technique then flow goes to step 622, at which the remaining capacity is estimated based on the estimated RBC. An exemplary Equation that can be used to estimate the remaining longevity at step 622 was discussed above, and thus, need not be repeated.

Returning to the discussion of step 608, if the answer to the determination at step 608 is Yes, meaning the battery of IMD is operating in a heavy battery usage and recovery period (UR period), then flow goes to step 620. At step 620 the RBC is estimated using a fourth technique which relies on historical battery data to estimate the RBC, since the present BV (aka current BV) is not indicative of the RBC when the battery is operating in a UR period, as can be appreciated from FIG. 5. In certain such embodiments, during a UR period (during which a current battery voltage ($BV_{current}$) is not indicative of the RBC), the RBC is estimated based on a most recent instance of the historical battery data (which was stored prior to the UR period, and thus was unaffected by the UR period) and based on the consumption between a time of the most recent instance of the historical battery data (that was unaffected by the UR period) and a current (i.e., present) time. After the RBC is estimated at step 620 using the fourth technique then flow goes to step 622, at which the remaining capacity is estimated based on the estimated RBC. An exemplary Equation that can be used to estimate the remaining longevity at step 622 was discussed above, and thus, need not be repeated.

Figure 7:
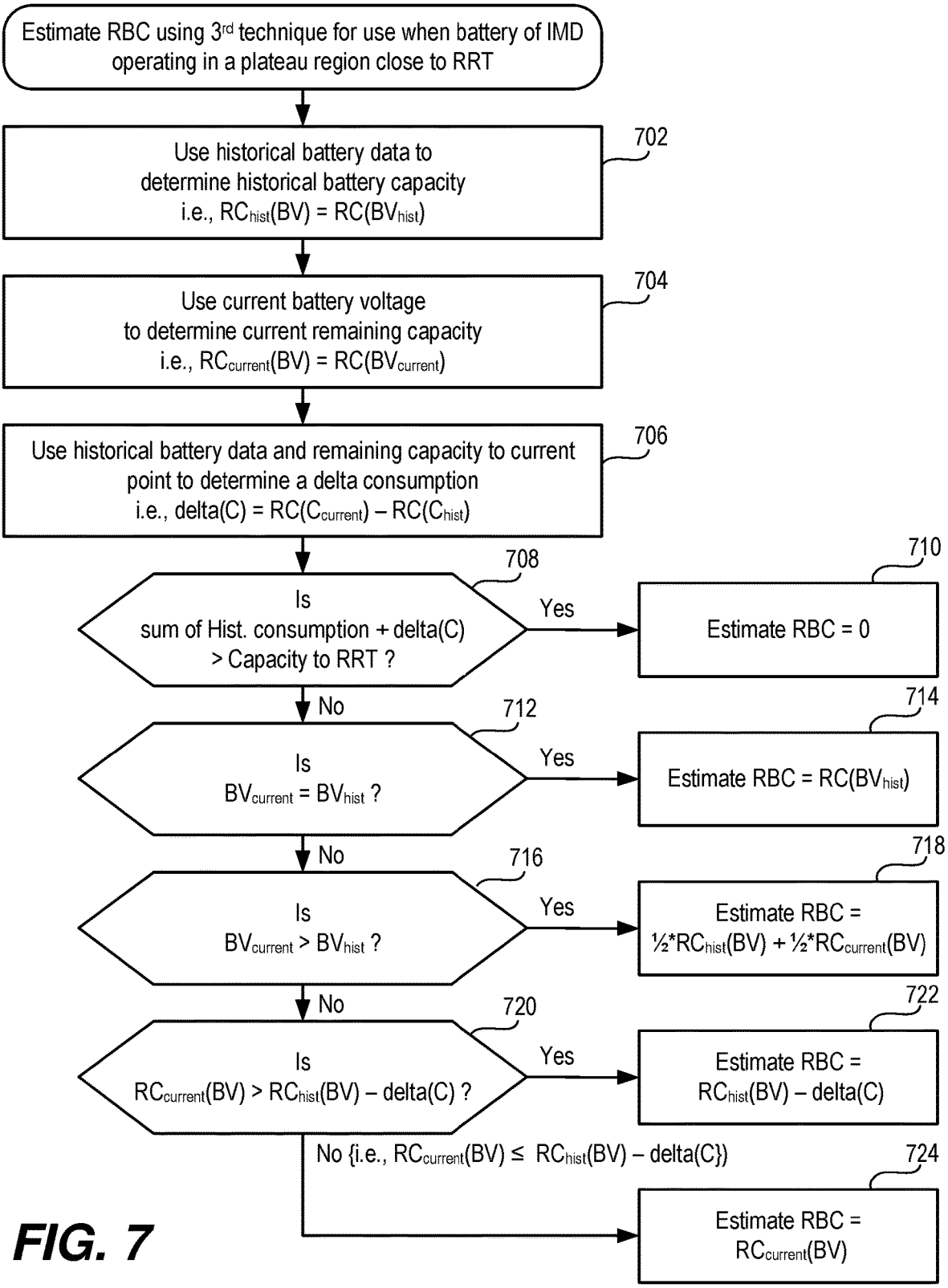
FIG. 7 is a high level flow diagram that provides additional details of one of the steps introduced in FIG. 6, according to certain embodiments of the present technology.

The high level flow diagram of FIG. 7 will now be used to provide additional details of step 616, introduced above in the discussion FIG. 6, according to certain embodiments of the present technology. As noted above, step 616 is performed when the BV is operating in a plateau and close to the RRT. Referring to FIG. 7, at step 702 historical battery data is used to determine historical battery capacity, and more specifically, it is assumed that the historical remaining capacity as a function of the present BV is equal to the remaining capacity as a function of the historical BV, i.e., $RC_{hist}(BV)=RC(BV_{hist})$.

At step 704 the current (i.e., present) battery voltage (BV) is used to determine a current remaining capacity (RC), i.e., $RC_{current}(BV)=RC(BV_{current})$.

At step 706, historical battery data and a remaining capacity to a current (i.e., present) point in time are used to determine a delta consumption, i.e., $delta(C)=RC(C_{current})-RC(C_{hist})$.

At step 708 there is a determination of whether a sum of the historical consumption plus the delta(C) is greater than the capacity to RRT (or more than a specified margin to RRT, e.g., outside the PSP region). If the answer to the determination at step 708 is Yes, then flow goes to step 710 and the estimated RBC is determined to be zero or within the specified margin to RRT, in which case an alert can be triggered to indicate that the IMD is within the PSP region near RRT or at RRT, and the device is to be replaced immediately or within a specified amount of time in the near future, or the battery of the IMD should be recharged if that is possible. If the answer to the determination of step 708 is No, then flow goes to step 712.

At step 712 there is a determination of whether the current battery voltage (i.e., $BV_{current}$) is equal to a most recently stored historical battery voltage (i.e., $BV_{hist}$). If the answer to the determination at step 712 is Yes, then flow goes to step 714 and the estimated RBC is determined to be equal to the remaining capacity as a function of a most recently stored historical battery voltage, i.e., at step 714 the estimated $RBC=RC(BV_{hist})$, which can be performed using a LUT and/or algorithm. If the answer to the determination of step 712 is No, then flow goes to step 716. Step 714 can be made more accurate by estimating the RBC to be equal to $RC(BV_{hist})$ minus the consumption since the $BV_{hist}$.

At step 716 there is a determination of whether the current battery voltage (i.e., $BV_{current}$) is greater than a most recently stored historical battery voltage (i.e., $BV_{hist}$). If the answer to the determination at step 716 is Yes, then flow goes to step 718 and the estimated RBC is determined to be equal to a summation of half the historical remaining capacity as a function of BV, plus half the current (i.e., present) remaining capacity as a function of BV, i.e., at step 718 the estimated $RBC=\frac{1}{2}*RC_{hist}(BV)+\frac{1}{2}*RC_{current}(BV)$. If the answer to the determination of step 716 is No, then flow goes to step 720.

At step 720 there is a determination of whether the current battery voltage (i.e., $BV_{current}$) is greater than a historical remaining capacity as a function of BV minus the delta(C). If the answer to the determination at step 720 is Yes, then flow goes to step 722 and the estimated RBC is determined to be equal to the historical remaining capacity as a function of BV minus the delta(c), i.e., at step 722 the estimated $RBC=RC_{hist}(BV)-delta(C)$. If the answer to the determination of step 720 is No, then flow goes to step 724. At step 724 the RBC is estimated to be equal to the current (i.e., present) remaining capacity as a function of BV, i.e., at step 724 the estimated $RBC=RC_{current}(BV)$.

Depending upon the specific implementation, the order of the various steps shown in FIGS. 6 and 7 can be rearranged, and thus, embodiments are not intended to be limited to the order shown in FIGS. 6 and 7. It would also be possible that just subsets of the steps shown in FIGS. 6 and 7 be performed. Other variations of the methods summarized with reference to FIGS. 6 and 7 could be appreciated from the above discussion. For example, certain steps can be separated into multiple steps. Further, logic associated with certain determination can be modified yet still provide the same or similar results. For example, the determination at step 612 could alternatively be whether the BV less than or equal to the voltage threshold (and thus, close to the RRT), in which case the Yes and No branches can be reversed.

Figure 8:
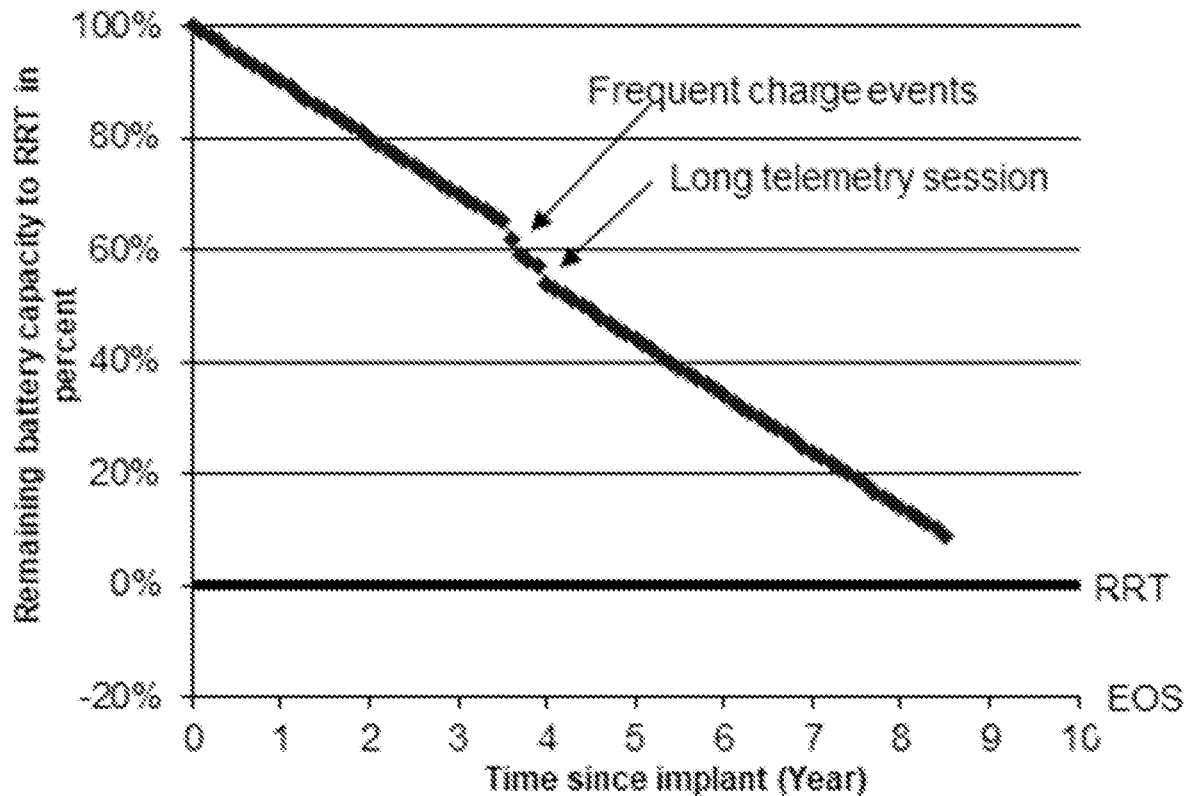
FIG. 8 illustrates an exemplary battery trending graph, produced in accordance with certain embodiments of the present technology, which trending graph can be displayed to a user via a display of an external device that wirelessly communicates with IMDs.

Exemplary performance profiles for exemplary IMD batteries were shown in FIGS. 2-5, which were discussed above. Such performance profiles can also be referred to as performance profile curves or battery voltage curves. Because of the complexity of such battery voltage curves, the presentation of battery voltage to a user can create user confusion, thus, making it difficult to present a true battery depletion using only battery voltage. Nevertheless, a battery voltage trend can provide useful information about the remaining longevity of a battery and IMD. Many medical practitioners and patients are used to checking battery depletion history using a battery voltage trend graph. This provides the medical practitioners and patients with confidence as how much capacity of a battery has been used and how much is remaining. Since the users are interested to see the battery depletion history and the health of the battery, certain embodiments of the present technology provide a remaining battery capacity trending graph to replace the traditional battery trending graph. Users expect to see a relative smooth curve if a patient does not require parameter changes that impact the battery consumption abruptly, such as pacing rate and/or pacing voltage changes. After a certain period of time, the curve itself will provide information as how long the battery will last. An example of such a trending curve is presented in FIG. 8. More specifically, FIG. 8 illustrates an exemplary battery trending graph, according to an embodiment of the present technology. Such a trending graph can be displayed to a user via a display of an external device that wirelessly communicates with an IMD. As can be appreciated from FIG. 8, certain events, such as frequency charging events and long telemetry sessions, may be represented in the trending graph. The trending graph may also show (and thus be useful for identifying) potential problems within an IMD when there are unexpected or unexplained steep drops in the remaining capacity to RRT, for example. More specifically, the trending graph can include one or more indications of when a period of heavy usage occurred and/or when a programming change occurred.

Figure 9:
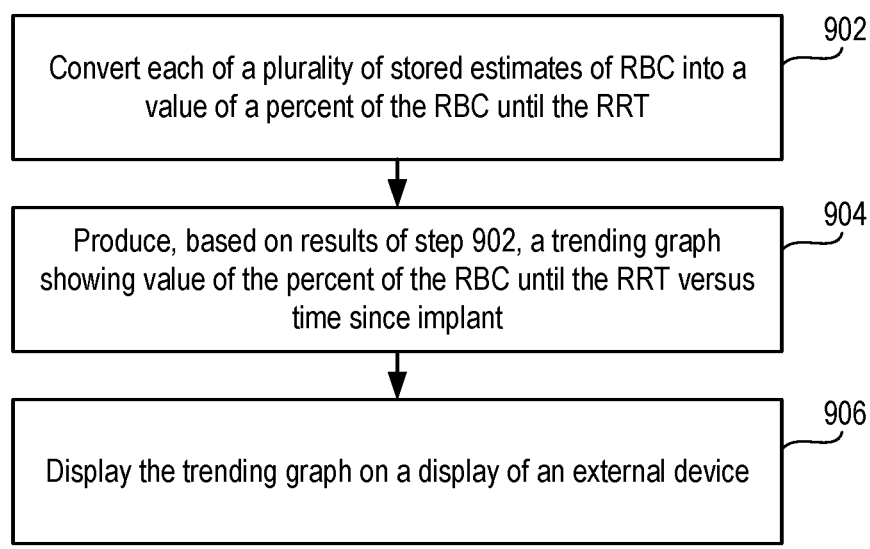
FIG. 9 is a high level flow diagram that is used to summarize a method for generating a trending graph, such as the trending graph shown in FIG. 8, in accordance with an embodiment of the present technology.

FIG. 9 is a high level flow diagram that is used to describe a method for generating a trending graph, such as the one shown in FIG. 8. Referring to FIG. 9, step 902 involves converting each of a plurality of stored estimates of RBC into a value of a percent of the RBC until the RRT. Step 904 involves producing, based on results of step 902, a trending graph showing values of the percent of the RBC until the RRT versus time since implant. Step 904 can also involve adding notations of potential interest to the trending graph, such as, but not limited to, one or more indications of when a period of heavy usage occurred and/or when a programming change occurred. Step 906 involves displaying the trending graph on a display of an external device.

Figure 10:
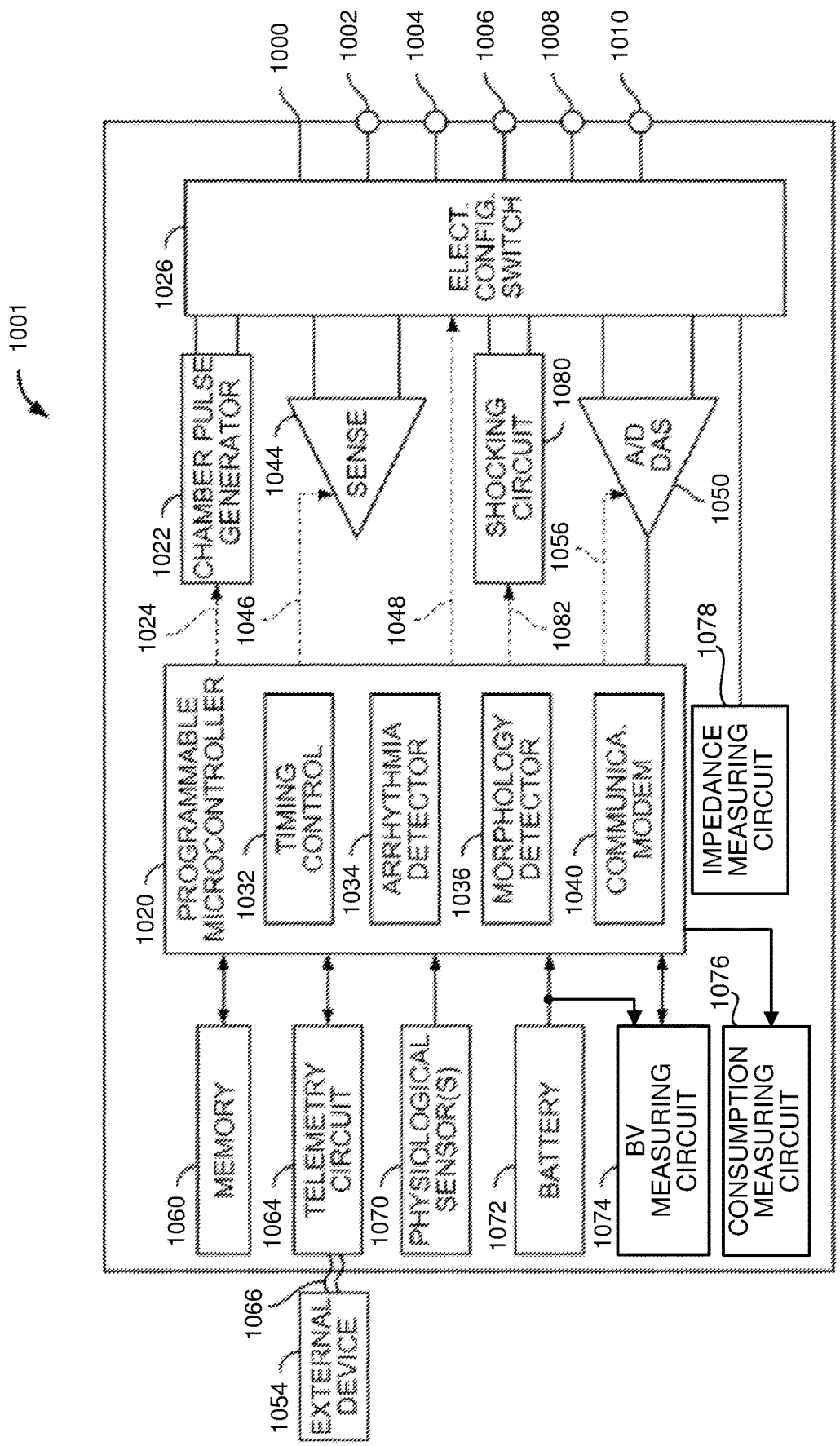
FIG. 10 shows a high level block diagram of one embodiment of an IMD for which remaining longevity can be estimated using embodiments of the present technology.

FIG. 10 shows a block diagram of one embodiment of an IMD 1001 that is implanted into the patient as part of the implantable system in accordance with certain embodiments herein. More specifically, the IMD 1001 is an example of an IMD for which the remaining longevity can estimated using embodiments of the present technology described herein. The IMD 1001 can be, for example, a pacemaker that is configured to be implanted in a pectoral region of a patient, a leadless pacemaker configured to be implanted within or attached to a cardiac chamber of a patient's heart, an ICD, or a patient monitoring device that does not provide therapy, but is not limited thereto. Certain components of the IMD 1001 shown in FIG. 10 can be eliminated if the features performed by such components are not needed, as would be the case if the IMD was a patient monitoring device that does not provide therapy. It would also be possible for the IMD 1001 to include additional components that are not shown in FIG. 10, as would be appreciated by one of ordinary skill in the art. It would also be possible for embodiments of the present technology to be used with IMDs that are not cardiac stimulation type devices, but rather, are neurostimulation devices, such as, but not limited to, spinal cord stimulation (SCS) devices, or deep brain stimulation (DBS) devices.

Referring to FIG. 10, the IMD 1001 has a housing 1000 to hold the electronic/computing components. Housing 1000 (which is often referred to as the "can", "case", "encasing", or "case electrode") may be programmably selected to act as the return electrode for certain stimulus modes. Housing 1000 may further include a connector (not shown) with a plurality of terminals 1002, 1004, 1006, 1008, and 1010. The terminals may be connected to electrodes that are located in various locations on housing 1000 or elsewhere within and about the heart. The IMD 1001 includes a programmable microcontroller 1020 that controls various operations of the IMD 1001, including cardiac monitoring and stimulation therapy. Microcontroller 1020 includes a microprocessor (or equivalent control circuitry), RAM and/or ROM memory, logic and timing circuitry, state machine circuitry, and I/O circuitry.

The IMD 1001 further includes a first pulse generator 1022 that generates stimulation pulses for delivery by one or more electrodes coupled thereto. Pulse generator 1022 is controlled by microcontroller 1020 via control signal 1024. Pulse generator 1022 may be coupled to the select electrode(s) via an electrode configuration switch 1026, which includes multiple switches for connecting the desired electrodes to the appropriate I/O circuits, thereby facilitating electrode programmability. Switch 1026 is controlled by a control signal 1028 from microcontroller 1020.

In the embodiment of FIG. 10, a single pulse generator 1022 is illustrated. Optionally, the IMD may include multiple pulse generators, similar to pulse generator 1022, where each pulse generator is coupled to one or more electrodes and controlled by microcontroller 1020 to deliver select stimulus pulse(s) to the corresponding one or more electrodes.

Microcontroller 1020 is illustrated as including timing control circuitry 1032 to control the timing of the stimulation pulses (e.g., pacing rate, atrio-ventricular (AV) delay, atrial interconduction (A-A) delay, or ventricular interconduction (V-V) delay, etc.). Timing control circuitry 1032 may also be used for the timing of refractory periods, blanking intervals, noise detection windows, evoked response windows, alert intervals, marker channel timing, and so on. Microcontroller 1020 also has an arrhythmia detector 1034 for detecting arrhythmia conditions and a morphology detector 1036. Although not shown, the microcontroller 1020 may further include other dedicated circuitry and/or firmware/software components that assist in monitoring various conditions of the patient's heart and managing pacing therapies.

The IMD 1001 is further equipped with a communication modem (modulator/demodulator) 1040 to enable wireless communication with the remote slave pacing unit. Modem 1040 may include one or more transmitters and two or more receivers as discussed herein in connection with FIG. 1B. In one implementation, modem 1040 may use low or high frequency modulation. As one example, modem 1040 may transmit i2i messages and other signals through conductive communication between a pair of electrodes. Modem 1040 may be implemented in hardware as part of microcontroller 1020, or as software/firmware instructions programmed into and executed by microcontroller 1020. Alternatively, modem 1040 may reside separately from the microcontroller as a standalone component.

The IMD 1001 includes a sensing circuit 1044 selectively coupled to one or more electrodes, that perform sensing operations, through switch 1026 to detect the presence of cardiac activity in the right chambers of the heart. Sensing circuit 1044 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 1026 determines the sensing polarity of the cardiac signal by selectively closing the appropriate switches. In this way, the clinician may program the sensing polarity independent of the stimulation polarity.

The output of sensing circuit 1044 is connected to microcontroller 1020 which, in turn, triggers or inhibits the pulse generator 1022 in response to the presence or absence of cardiac activity. Sensing circuit 1044 receives a control signal 1046 from microcontroller 1020 for purposes of controlling the gain, threshold, polarization charge removal circuitry (not shown), and the timing of any blocking circuitry (not shown) coupled to the inputs of the sensing circuitry.

In the embodiment of FIG. 10, a single sensing circuit 1044 is illustrated. Optionally, the IMD may include multiple sensing circuits, similar to sensing circuit 1044, where each sensing circuit is coupled to one or more electrodes and controlled by microcontroller 1020 to sense electrical activity detected at the corresponding one or more electrodes. Sensing circuit 1044 may operate in a unipolar sensing configuration or in a bipolar sensing configuration.

The IMD 1001 further includes an analog-to-digital (A/D) data acquisition system (DAS) 1050 coupled to one or more electrodes via switch 1026 to sample cardiac signals across any pair of desired electrodes. Data acquisition system 1050 is configured to acquire intracardiac electrogram signals, convert the raw analog data into digital data, and store the digital data for later processing and/or telemetric transmission to an external device 1054 (e.g., a programmer, local transceiver, or a diagnostic system analyzer). Data acquisition system 1050 is controlled by a control signal 1056 from the microcontroller 1020.

Microcontroller 1020 is coupled to a memory 1060 by a suitable data/address bus. The programmable operating parameters used by microcontroller 1020 are stored in memory 1060 and used to customize the operation of the IMD 1001 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 1001 may be non-invasively programmed into memory 1060 through a telemetry circuit 1064 in telemetric communication via communication link 1066 with external device 1054. Telemetry circuit 1064 allows intracardiac electrograms and status information relating to the operation of IMD 1001 (as contained in microcontroller 1020 or memory 1060) to be sent to external device 1054 through communication link 1066. The external device 1054 can estimate a remaining longevity of the IMD 1001. In accordance with certain embodiments, the memory 1060 can store historical battery data, examples of which were discussed above in the discussion of FIGS. 6 and 7.

The IMD 1001 can further include magnet detection circuitry (not shown), coupled to microcontroller 1020, to detect when a magnet is placed over the unit. A magnet may be used by a clinician to perform various test functions of the IMD 1001 and/or to signal microcontroller 1020 that external device 1054 is in place to receive or transmit data to microcontroller 1020 through telemetry circuits 1064.

The IMD 1001 can further include one or more physiological sensors 1070. Such sensors are commonly referred to as "rate-responsive" sensors because they are typically used to adjust pacing stimulation rates according to the exercise state of the patient. However, physiological sensor 1070 may further be used to detect changes in cardiac output, changes in the physiological condition of the heart, or diurnal changes in activity (e.g., detecting sleep and wake states). Signals generated by physiological sensors 1070 are passed to microcontroller 1020 for analysis. Microcontroller 1020 responds by adjusting the various pacing parameters (such as rate, AV Delay, V-V Delay, etc.) at which the atrial and ventricular pacing pulses are administered. While shown as being included within the IMD 1001, physiological sensor(s) 1070 may be external to the IMD 1001, yet still be implanted within or carried by the patient. Examples of physiologic sensors might include sensors that, for example, sense respiration rate, pH of blood, ventricular gradient, activity, position/posture, minute ventilation (MV), and so forth.

A battery 1072 provides operating power to all of the components in IMD 1001. Battery 1072 is preferably capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 1072 also desirably has a predictable discharge characteristic so that elective replacement time can be detected. As one example, IMD 1001 employs lithium/silver vanadium oxide batteries. Exemplary performance profile curves for various different types of batteries, which can be used as the battery 1072, are shown in and were described above with reference to FIGS. 2-5. At any given time, the battery 1072 will have a battery voltage (BV) and a remaining battery capacity (RBC). The BV can be measured, e.g., by a BV measurement circuit 1074 of the MD 1001. The IMD 1001 can also include a consumption measurement circuit 1076 that can keep track of consumed housekeeping current, consumed pacing current, consumed sensing current, consumed capacitor maintenance current, consumed battery maintenance current, consumed telemetry current, and/or the like.

The IMD 1001 further includes an impedance measuring circuit 1078, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 1078 is coupled to switch 1026 so that any desired electrode may be used. In this embodiment the IMD 1001 further includes a shocking circuit 1080 coupled to microcontroller 1020 by a data/address bus 1082.

Figure 11:
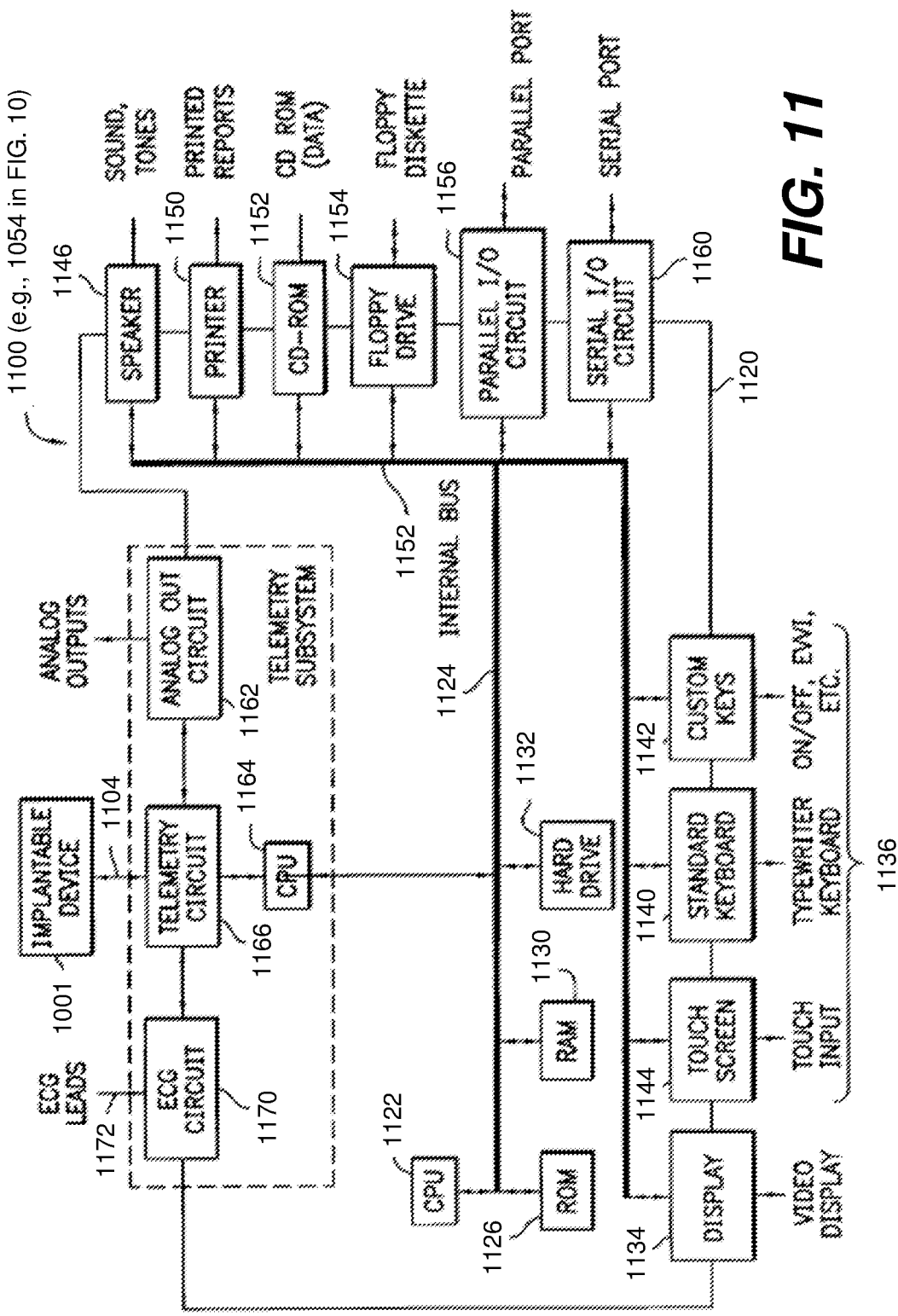
FIG. 11 shows a high level block diagram of one embodiment of an external device that can be used to determine and display estimates of remaining longevity for IMDs in wireless communication with the external device, in accordance with certain embodiments of the present technology.

FIG. 11 is a functional block diagram of one embodiment of an external device 1100 that can determine estimates of the remaining longevity for one or more types of IMDs using embodiments of the present technology described herein. The external device 1100 can be, e.g., a clinical programmer, a remote patient monitor, or a portable computing device, such as a smartphone, a tablet computer, or a laptop computer, but is not limited thereto. Embodiments of the present technology can also be used with other types of external devices that can wireless communication with IMDs in order to obtain measures of BV and stored historical data, and/or the like from IMDs.

Referring to FIG. 11, the external device 1100 illustrating greater details thereof. A CPU 1122 is in communication with an internal bus 1124. The internal bus 1124 provides a common communication link and power supply between the various electrical devices of the external device 1100, including the CPU 1122. The external device 1100 also comprises memory and storage including ROM 1126, RAM 1130, and a hard drive 1132 in communication with the internal bus 1124. The ROM 1126, RAM 1130, and hard drive 1132 provide temporary memory and non-volatile storage of data in a well-known manner. In particular, the ROM 1126, RAM 1130, and hard drive 1132 can store programmed control programs and commands for upload to the IMD 1001 as well as control programs for display of data received from the IMD 1001 as is well understood in the art. It will be appreciated that, in certain embodiments, alternative data storage/memory devices, such as flash memory, can be included or replace at least one of the ROM 1126, RAM 1130, and hard drive 1132 without detracting from the spirit of the invention.

The external device 1100 also comprises a display 1134. The display 1134 is adapted to visually present graphical and alphanumeric data in a manner well understood in the art. For example, the display 1134 can be used to display estimates of remaining longevity for an IMD, but is not limited thereto.

In certain embodiments, the external device 1100 also comprises input devices 136 comprising, in this embodiment, a keyboard 1140, a plurality of custom keys 1142, and a touchscreen 1144 aspect of the display 1134. The keyboard 1140 facilitates entry of alphanumeric data into the programmer system 1100. The custom keys 1142 are programmable in order to provide one touch functionality of predefined functions and/or operations of the external device 1100. The custom keys 1142 may be embodied as dedicated touch keys and/or as predefined areas of the touchscreen 1144.

In certain embodiments, the external device 1100 also comprises a speaker 1146 and a printer 1150 in communication with the internal bus 1124. The speaker 1146 is adapted to provide audible alerts and signals to a user and the printer 1150 is adapted to provide a printed read-out of information as generated or monitored by the external device 1100.

The external device 1100 can also comprise a CD drive 1152 and a floppy drive 1154 which together provide removable storage of data. The CD drive 1152 and the floppy drive 1154 provide removable data storage and read capability for the programmer system 1100 in a well understood manner.

In this embodiment, the external device 1100 also includes a parallel input-output (IO) circuit 1156, a serial IO circuit 1160, and an analog output circuit 1162. These circuits 1156, 1160, 1162 provide a variety of communication capability with other devices in a manner well understood in the art.

In this embodiment, the external device 1100 further includes a telemetry CPU 1164 that is in communication with a telemetry circuit 1166. The telemetry circuit 1166 maintains the communication link 1104 between the external device 1100 and the IMD 1001. This aspect of the invention enables the external device 1100 and the IMD 1001 to exchange information at an increased speed to enable real-time transmission of signals obtained from the at least physiological sensor 1108.

In the example shown, the external device 1100 also comprises an ECG circuit 1170 in communication with a plurality of ECG leads 1172. The ECG circuit 1170 and the ECG leads 1172 obtain electrical signals from the surface of a patient's body in a well understood manner and configure these signals for display as an ECG waveform 1174 on the display 1134 of the external device 1100.

It is to be understood that the components of the external device 1100 described above are exemplary and that additions or deletions of certain elements may be made without detracting from the spirit of the invention.

Another function that is provided, in certain embodiments, by the input devices 1136 includes access to an automatic physician follow-up diagnostic to verify/monitor IMD operation, patient condition, records of past anomalous cardiac events, records of therapy provided, implantable device battery charge state, etc. The input devices 1136 can also provide up-down scrolling through available functions or operations as well as selection of available functions.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for estimating a remaining longevity of an implantable medical device (IMD) powered by a battery that at any given time has a battery voltage (BV) and a remaining battery capacity (RBC), wherein performance profile information for the battery specifies a relationship between the BV and the RBC including specifying one or more decline regions and one or more plateau regions, wherein within each of the one or more decline regions a rate at which the BV decreases as the RBC decreases exceeds a rate threshold, and wherein within each of the one or more plateau regions the rate at which the BV decreases as the RBC decreases does not exceed the rate threshold, and each of the decline and each of the plateau regions has a corresponding battery voltage range ($BV_{range}$), the method comprising:
- determining whether the battery is operating within one of the one or more plateau regions, or is operating within one of the one or more decline regions, by measuring the BV and determining which one of the corresponding battery voltage ranges the BV is within;
- estimating the RBC using a first technique when it is determined based on the BV that the battery is operating within one of the one or more plateau regions, and the BV is above a voltage threshold, wherein the BV being above the voltage threshold is indicative of the IMD being far from a recommended replacement time (RRT);
- estimating the RBC using a second technique, that differs from the first technique, when it is determined based on the BV that the battery is operating within one of the two one or more decline regions;
- estimating the RBC using a third technique, that differs from the first and second techniques, when the battery is operating within one of the one or more plateau regions and the BV is below the voltage threshold, wherein the BV being below the voltage threshold is indicative of the IMD being close to the RRT; and
- estimating the remaining longevity of the IMD based on at least one of the estimates of the RBC.

2. The method of claim 1, wherein:
using the first technique to estimate the RBC comprises estimating the RBC based on a weighted average of a remaining capacity as a function of the BV and a remaining capacity as a function of consumption; and
using the second technique to estimate the RBC comprises estimating the RBC based on the remaining capacity as a function of consumption.

3. The method of claim 2, wherein:
the battery voltage range for each of the one or more decline regions and each of the one or more plateau regions extends from a respective start of the battery voltage range ($BV_{start\ of\ range}$) to a respective end of the battery voltage range ($BV_{end\ of\ range}$); and
the estimating the RBC based on the weighted average of the remaining capacity as a function of the BV and the remaining capacity as a function of consumption is performed using the following equation:

$$RBC = \frac{(BV - BV_{end\ of\ range}) * RC(C) + (BV_{start\ of\ range} - BV) * RC(BV)}{BV_{range}}$$

where
RBC is the remining battery capacity,
RC(BV) is the remining capacity as a function of the BV,
RC(C) is the remining capacity as a function of consumption,
$BV_{start\ of\ the\ range}$ is the BV at the start of the $BV_{range}$,
$BV_{end\ of\ the\ range}$ is the BV at the end of the $BV_{range}$, and
$BV_{range}$ is a voltage difference between the $BV_{start\ of\ the\ range}$ and the $BV_{end\ of\ the\ range}$.

4. The method, of claim 3, wherein:
the estimating the RBC based on the remaining capacity as a function of consumption (RC(C)) is performed using the following equation:

RBC=RC(BV)

where
RBC is the remining battery capacity, and
RC(BV) is the remining capacity as a function of the BV.

5. The method, of claim 3, wherein the consumption comprises an initial capacity minus a used capacity, and wherein the used capacity comprises a summation of the following:
consumption during manufacturing and testing;
consumption during shelf-time;
consumption during implant; and
consumption postimplant to a present date.

6. The method of claim 2, wherein:
the IMD stores historical battery data from time-to-time, the historical battery data including at least one of a historical battery voltage ($BV_{hist}$) or a historical remaining battery capacity ($RC_{hist}$); and
using the third technique to estimate the RBC comprises estimating the RBC based on the stored historical battery data.

7. The method of claim 6, wherein:
using the third technique to estimate the RBC further comprises determining current battery data, the current battery data including at least one of a current battery voltage ($BV_{current}$) or a current remaining capacity ($RC_{current}$), and estimating the RBC also based on the current battery data.

8. The method of claim 1, further comprising:
storing historical battery data from time-to-time, the historical battery data including at least one of a historical battery voltage ($BV_{hist}$) or a historical remaining battery capacity ($RC_{hist}$);
identifying when the battery is operating in a heavy battery usage and recovery period, which is a period during and following which the battery is used for one or more predetermined functions that cause the BV to temporarily drop for a length of time before recovering, with an extent of the length of time being dependent upon which type of the one or more predetermined functions the battery was used for; and
during an instance of the heavy battery usage and recovery period, estimating the RBC using a further technique where the RBC is estimated based on a most recent instance of the historical battery data, which was stored prior to the heavy battery usage and recovery period, and based on a consumption between a time of the most recent instance of the historical battery data and a current time;
wherein during each instance of the heavy battery usage and recovery period, the RBC is estimated without using a measure of the BV that coincides with the heavy battery usage and recovery period.

9. The method of claim 1, wherein the estimating the remaining longevity of the IMD based on at least one of the estimates of the RBC comprises:
estimating a total future consumption; and
estimating the remaining longevity of the IMD using the following equation:

$$\text{remaining longevity} = \frac{RBC}{\text{Future (use)}}$$

where
remaining longevity is the remaining longevity of the IMD,
RBC is a most recent estimate of the RBC; and
Future (use) is the estimated total future consumption.

10. The method of claim 1, wherein the method is performed by an external device that wirelessly communicates with the IMD for which the remaining longevity is being estimated.

11. The method of claim 10, further comprising:
producing and displaying, on a display of the external device, a trending graph that shows the estimated RBC at a plurality of different times verses a time since implant of the IMD.

12. An external device configured to estimate a remaining longevity of an implantable medical device (IMD) powered by a battery that at any given time has a battery voltage (BV) and a remaining battery capacity (RBC), wherein performance profile information for the battery specifies a relationship between the BV and the RBC including specifying one or more decline regions and one or more plateau regions, wherein within each of the one or more decline regions a rate at which the BV decreases as the RBC decreases exceeds a rate threshold, and wherein within each of the one or more plateau regions the rate at which the BV decreases as the RBC decreases does not exceed the rate threshold, the external device comprising:
a telemetry subsystem configured to wirelessly communicate with an IMD and thereby obtain measurements of the BV from the IMD;
at least one processor communicatively coupled to the telemetry subsystem and configured to
determine whether the battery of the IMD is operating within a said plateau region or a said decline region based on a measurement of the BV obtained from the IMD;
estimate the RBC using a first technique when it is determined based on the BV that the battery of the IMD is operating within one of the one or more plateau regions, and the BV is above a voltage threshold, wherein the BV being above the voltage threshold is indicative of the IMD being far from a recommended replacement time (RRT);
estimate the RBC using a second technique, that differs from the first technique, when it is determined based on the BV that the battery of the IMD is operating within one of the one or more decline regions;
estimate the RBC using a third technique, that differs from the first and second techniques, when the battery is operating within one of the one or more plateau regions and the BV is below the voltage threshold, wherein the BV being below the voltage threshold is indicative of the IMD being close to the RRT; and
estimate the remaining longevity of the IMD based on at least one of the estimates of the RBC; and
a user interface configured to display or otherwise output the estimate of the remaining longevity of the IMD.

13. The external device of claim 12, further comprising memory, and wherein the at least one processor is configured to:
store historical battery data in the memory from time-to-time, the historical battery data including at least one of a historical battery voltage ($BV_{hist}$) or a historical remaining battery capacity ($RC_{hist}$);
identify when the battery is operating in a heavy battery usage and recovery period, which is a period during and following which the battery is used for one or more predetermined functions that cause the BV to temporarily drop for a length of time before recovering, with an extent of the length of time being dependent upon which type of the one or more predetermined functions the battery was used for;
detect occurrences of the heavy battery usage and recovery period; and
during a detected occurrence of the heavy battery usage and recovery period, estimate the RBC using a further technique where the RBC is estimated based on a most recent instance of the historical battery data, which was stored in the memory prior to the heavy battery usage and recovery period, and based on a consumption between a time of the most recent instance of the historical battery data and a current time.

14. The external device of claim 12, wherein the external device is selected from the group consisting of:
an external clinical programmer;
an in-home monitor; or
a mobile computing device.

15. The external device of claim 12, wherein the user interface comprises a display and wherein the at least one processor is configured to produce and display, on the display of the external device, a trending graph that shows the estimated RBC at a plurality of different times verses a time since implant of the IMD, wherein the trending graph includes one or more indications of when a period of heavy usage occurred or when a programming change occurred.

16. The external device of claim 12, wherein the at least one processor is configured to:
estimate a total future consumption; and
estimate the remaining longevity of the IMD using the following equation:

$$\text{remaining longevity} = \frac{RBC}{\text{Future (use)}}$$

where
remaining longevity is the remaining longevity of the IMD,
RBC is a most recent estimate of the RBC; and
Future (use) is the estimated total future consumption.

17. A method for estimating a remaining longevity of an implantable medical device (IMD) powered by a battery, wherein performance profile information for the battery specifies a relationship between a battery voltage (BV) and a remaining battery capacity (RBC), including specifying one or more decline regions and one or more plateau regions, with each of the decline and each of the plateau regions having a corresponding battery voltage range ($BV_{range}$), the method comprising:
(a) obtaining a battery voltage (BV) measurement of the battery that powers the IMD;
(b) determining, based on the BV measurement and the performance profile information for the battery, whether the battery is operating in a said decline region or a said plateau region;

(c) estimating the RBC
  (c.i) using a first technique when the battery is operating within a said plateau region and the BV measurement is above a voltage threshold indicative of the IMD being far from a recommended replacement time (RRT);
  (c.ii) using a second technique when the battery is operating within a said decline region;
  (c.iii) using a third technique when the battery is operating a said plateau region and the BV measurement is below the voltage threshold indicative of the IMD being close to the RRT; and
  (c.iv) using a fourth technique when the battery is operating in a heavy battery usage and recovery period, which is a period during and following which the battery is used for one or more predetermined functions that cause the BV to temporarily drop for a length of time before recovering; and
(d) estimating the remaining longevity of the IMD based on a most recent estimate of the RBC;
wherein steps (a), (b), (c), and (d) are repeated over time such that each of the first, second, third and fourth techniques, which differ from one another, is used to estimate the RBC one or more times.

18. The method of claim 17, wherein:
using the first technique to estimate the RBC comprises estimating the RBC based on a weighted average of a remaining capacity as a function of the BV and a remaining capacity as a function of consumption;
using the second technique to estimate the RBC comprises estimating the RBC based on the remaining capacity as a function of consumption;
using the third technique to estimate the RBC comprises estimating the RBC based on a most recent instance of stored historical battery data and based on a remaining capacity; and
using the fourth technique to estimate the RBC comprises estimating the RBC based on a most recent instance of the historical battery data, which was stored in memory prior to a heavy battery usage and recovery period, and based on a consumption between a time of the most recent instance of the historical battery data and a current time.

19. A method for estimating a remaining longevity of an implantable medical device (IMD) powered by a battery, wherein performance profile information for the battery specifies a relationship between a battery voltage (BV) and a remaining battery capacity (RBC), including specifying one or more decline regions and one or more plateau regions, with each of the decline regions and each of the plateau regions having a corresponding battery voltage range, the method comprising:

estimating the RBC from time-to-time, which includes
  using a first technique to estimate the RBC when the battery is operating within one of the one or more plateau regions;
  using a second technique to estimate the RBC when the battery is operating within one of the one or more decline regions; and
  using a further technique to estimate the RBC when the battery is operating in a heavy battery usage and recovery period, which is a period during and following which the battery is used for one or more predetermined functions that cause the BV to temporarily drop for a length of time before recovering;
  wherein the first, second and further techniques differ from one another; and
estimating the remaining longevity of the IMD from time-to-time, wherein each time the remaining longevity is estimated the remaining longevity is estimated based on a most recent estimate of the RBC.

20. The method of claim 19, further comprising:
storing historical battery data from time-to-time, the historical battery data including at least one of a historical battery voltage ($BV_{hist}$) or a historical remaining battery capacity ($RC_{hist}$); and
wherein using the further technique to estimate the RBC, when the battery is operating in a said heavy battery usage and recovery period, comprises estimating the RBC based on a most recent instance of the historical battery data, which was stored prior to the heavy battery usage and recovery period, and based on a consumption between a time of the most recent instance of the historical battery data and a current time.

21. The method of claim 20, wherein during each instance of the heavy battery usage and recovery period, the RBC is estimated without using a measure of the BV that coincides with the heavy battery usage and recovery period.

22. The method of claim 19, wherein:
the first technique is used to estimate the RBC when the battery is operating within one of the one or more plateau regions and the BV is above a voltage threshold, wherein the BV being above the voltage threshold is indicative of the IMD being far from a recommended replacement time (RRT); and
the estimating the RBC from time-to-time further includes using a third technique to estimate the RBC, when the battery is operating within one of the one or more plateau regions and the BV is below the voltage threshold, wherein the BV being below the voltage threshold is indicative of the IMD being close to the RRT, and wherein the third technique differs from the first, second and further techniques.

* * * * *